US006852842B2

(12) United States Patent
Brechbiel et al.

(10) Patent No.: US 6,852,842 B2
(45) Date of Patent: Feb. 8, 2005

(54) METHODS FOR FUNCTIONAL KIDNEY IMAGING USING SMALL DENDRIMER CONTRAST AGENTS

(75) Inventors: Martin W. Brechbiel, Annandale, VA (US); Robert A. Star, Bethesda, MD (US); Hisataka Kobayashi, Nishinomiya (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 58 days.

(21) Appl. No.: 10/229,316

(22) Filed: Aug. 26, 2002

(65) Prior Publication Data

US 2004/0037777 A1 Feb. 26, 2004

(51) Int. Cl.$^7$ .................................................. C07F 5/00
(52) U.S. Cl. ......................... 534/15; 424/1.11; 424/9.1; 424/9.36
(58) Field of Search .............................. 424/1.11, 1.65, 424/9.1, 9.3, 9.36, 9.361, 9.362; 534/7, 10–16

(56) References Cited

U.S. PATENT DOCUMENTS

| 5,338,532 A | 8/1994 | Tomalia et al. |
| 5,527,524 A | 6/1996 | Tomalia et al. |
| 5,759,518 A | 6/1998 | Schmitt-Willich et al. |
| 5,834,020 A | 11/1998 | Margerum et al. |
| 5,914,095 A | 6/1999 | Watson |

FOREIGN PATENT DOCUMENTS

| EP | 0736059 B1 | 12/1994 |
| WO | WO 93/06868 | 4/1993 |
| WO | WO 93/14147 | 7/1993 |
| WO | WO95/17451 | 6/1995 |
| WO | WO00/72037 | 11/2000 |

OTHER PUBLICATIONS

Kobayashi et al., "Dynamic Micro–Magnetic Resonance Imaging of Liver Micrometastasis in Mice with a Novel Liver Macromolecular Magnetic Resonance Contrast Agent DAB–Am64–(1B4M–Gd)$_{64}$," *Cancer Research*, vol. 61, pp. 4966–4970, Jul. 1, 2001.

Kobayashi et al., "Monoclonal antibody–dendrimer conjugates enable radiolabeling of antibody with markedly high specific activity with minimal loss of immunoreactivity," *European Journal of Nuclear Medicine*, vol. 27, No. 9, Sep. 2000.

Tajarobi et al., "Transport of poly amidoamine dendrimers across Madin–Darby canine kidney cells," *International Journal of Pharmaceutics*, vol. 215, pp. 263–267, (2001).

Eichman et al., "Imaging of gold dendrimer nanocomposites in cells," *Mat. Res. Soc. Symp. Proc.*, vol. 676, pp. Y9.3.1–Y9.3.11 (2001).

Konda, et al., "Specific targeting of folate–dendrimer MRI contrast agents to the high affinity folate receptor expressed in ovarian tumor xenografts," *Magnetic Resonance Materials in Physics, Biology and Medicine*, vol. 12, pp. 104–113 (2001).

Malik et al., "Dendrimer–platinate: a novel approach to cancer chemotherapy," *Anti–Cancer Drugs*, Vo. 10, pp. 767–776 (1999).

Caravan et al., "Gadolinium (III) Chelates as MRI Contrast Agents: Structure, Dynamics, and Applications," *Chem. Rev.*, pp. 2293–2352 (1999).

Kobayashi et al., "Macromolecular MRI Contrast Agents with Small Dendrimers: Pharmacokinetic Differences between Sizes and Cores," *Bioconjugate Chem.*, vol. 14, pp. 388–394 (2003).

Aldrich Handbook of Fine Chemicals and Laboratory Equipment, pp. 486 and 1521, (2000–2001).

Bourne, M.W., et al., "Evaluation of the Effects of Intravascular MR Contrast Media (Gadolinium Dendrimer) on 3D Time of Flight Magnetic Resonance Angiography of the Body," *JMRI*, pp 305–310, Mar.–Apr., (1995).

Bulte, J., et al., "Dysprosium–DOTA–PAMAM Dendrimers as Macromolecular T2 Contrast Agents," *Investigative Radiology*, vol. 33(11), pp 841–845, (1998).

Kobayashi, H., et al., "Comparison of the Macromolecular MR Contrast Agents with Ethylenediamine–Core versus Ammonia–Core Generation–6 Polyamidoamine Dendrimer," *Bioconjugate Chem.*, vol. 12(1), pp 100–107, (2001).

Kobayashi, H., et al., "Evaluation of the in Vivo Biodistribution of Indium–111 and Yttrium–88 Labeled Dendrimer–1B4M–DTPA and Its Conjugation with Anti–Tac Monoclonal Antibody," *Bioconjugate Chem.*, vol. 10(1), pp. 103–111, (1999).

Kobayashi, H., et al., "3D–Micro–MR Angiography of Mice Using Macromolecular MR Contrast Agents With Polyamidoamine Dendrimer Core With Reference to Their Pharmacokinetic Properties," *Magnetic Resonance in Medicine*, vol. 45, pp 454–460, (2001).

(List continued on next page.)

*Primary Examiner*—Dameron Levest Jones
(74) *Attorney, Agent, or Firm*—Klarquist Sparkman, LLP

(57) ABSTRACT

Small dendrimer-based MRI contrast agents are disclosed to accumulate in renal tubules. The accumulation enables visualization of renal structure and function, permitting assessment of structural and functional damage to the kidneys. In a disclosed embodiment, six, small dendrimer-based MRI contrast agents were synthesized, and their pharmacokinetics, whole body retention, and renal MRI images were evaluated in mice. Surprisingly, despite having unequal renal clearance properties, all of the dendrimer agents clearly visualized the renal anatomy and proximal straight tubules of the mice better than Gd-[DTPA]-dimeglumine. Dendrimer conjugate contrast agents prepared from PAMAM-G2D, DAB-G3D, and DAB-G2D dendrimers were excreted rapidly and may be acceptable for use in clinical applications.

49 Claims, 11 Drawing Sheets

OTHER PUBLICATIONS

Kobayashi, H., et al., "Micro–MR Angiography of Normal and Intratumoral Vessels in Mice Using Dedicated Intravascular MR Contrast Agnets with High Generation of Polyamidoamine Dendrimer Core: Reference to Pharmacokinetic Properties of Dendrimer–Based MR Contrast Agents," *J. Magnetic Resonance Imaging*, vol. 14, pp 705–713, (2001).

Kobayashi, H., et al., "Novel Intravascular Macromolecular MRI Contrast Agent With Generation–4 Polyamidoamine Dendrimer Core: Accerlated Renal Excretion With Coinjection of Lysine," *Magnetic Resonance in Medicine*, vol. 46, pp 457–464, (2001).

Kobayashi, H., et al., "Novel Liver Macromolecular MR Contrast Agent With a Polypropylenimine Diaminobutyl Dendrimer Core: Comparison to the Vascular MR Contrast Agent With the Polyamidoamine Dendrimer Core," *Magentic Resonance in Medicine*, vol. 46, pp 795–802, (2001).

Kobayashi, H., et al, "Positive Effects of Polyethylene Glycol Conjugation to Generation–4 Polyamidoamine Dendrimers as Macromolecular MR Contrast Agents," *Magnetic Resonance in Medicine*, vol. 46, pp. 781–788, (2000).

Kobayashi, H., et al., "Renal tubular damage detected by dynamic micro–MRI with a dendrimer–based magnetic resonance contrast agent," *Kidney International*, vol. 61, 1980–1985, (2002).

Malik, N., et al., "Dendrimers: Relationship Between Structure and Biocompatibility In Vitro, and Preliminary Studies on The Biodistribution of $^{125}$I–labelled polyamidoamine dendrimers in vivo," *J. Controlled Release*, vol. 65, pp 133–148, 2000.

Sato, N., et al., "Pharmacokinetics and Enhancement Patterns of Macromolecular MR Contrast Agent With Various Sizes of Polyamidoamine Dendrimer Cores," *Magnetic Resonance in Medicine*, vol. 46, pp 1169–1173, (2001).

Wiener, E.C., "Dendrimer–Based Metal Chelates: A New Class of Magnetic Resonance Imaging Contrast Agents," *MRM*, vol. 31, pp 1–8, 1994.

Wörner, D. and Mülhaupt, R., "Polynitrile– and Polyamine–Functional Poly(trimethylene imine) Dendrimers," *Angew. Chem. Int. Ed. Engl.*, vol. 32(9), pp 1306–1308 (1993).

Chang, R.L.S., et al., "Permselectivity of The Glomerular Capliiary Wall to Macromolecules—II. Experimental Studies in Rats Using Netural Dextran," *Biophysical Journal*, vol. 15, pp. 887–906 (1975).

Guasch, A. et al, "Charge Selectivity of the Glomerular Filtaration Barrier in Healthy and Nephrotic Humans," *J. Clin Invest.*, vol.. 92, pp. 2274–2282, (1993).

Kobayashi, H, et al, "The Pharmacokinetic Characteristics of Glycolated Humanized Anti–Tacs Fabs are Determined by Their Isoelectric Points," *Cancer Research*, vol. 59, pp. 422–430, (1999).

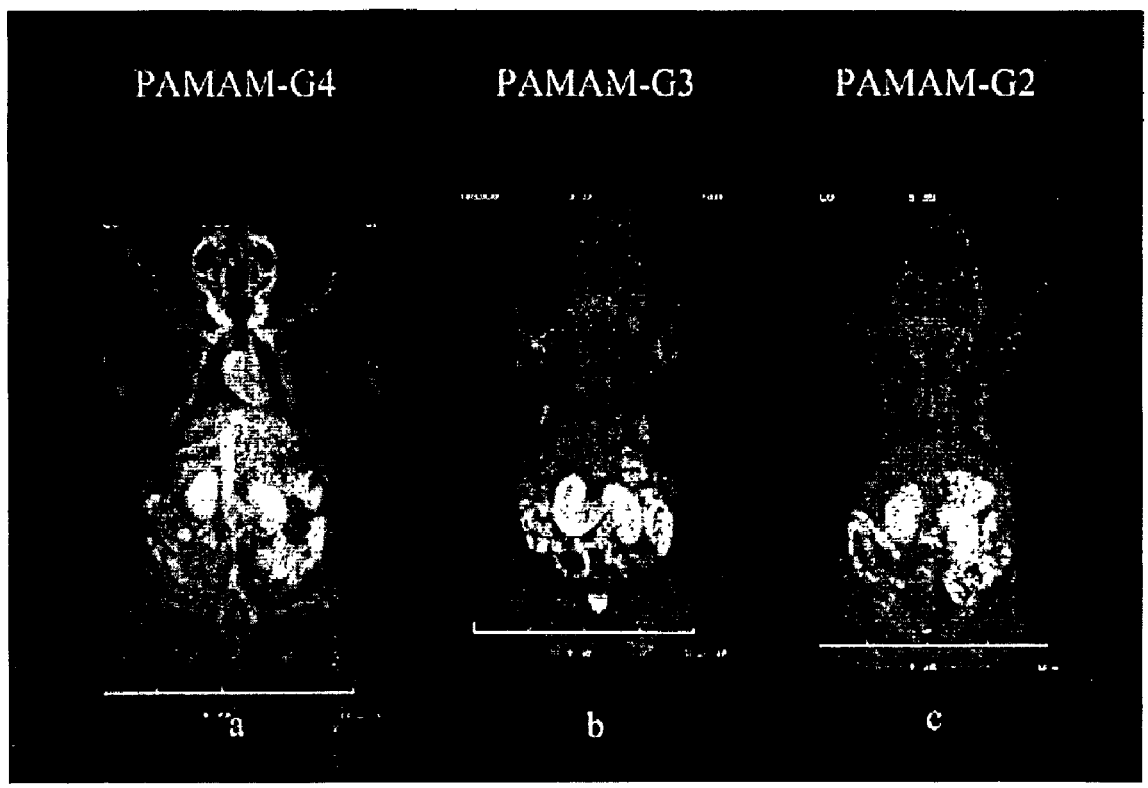
FIGS. 4 a-c

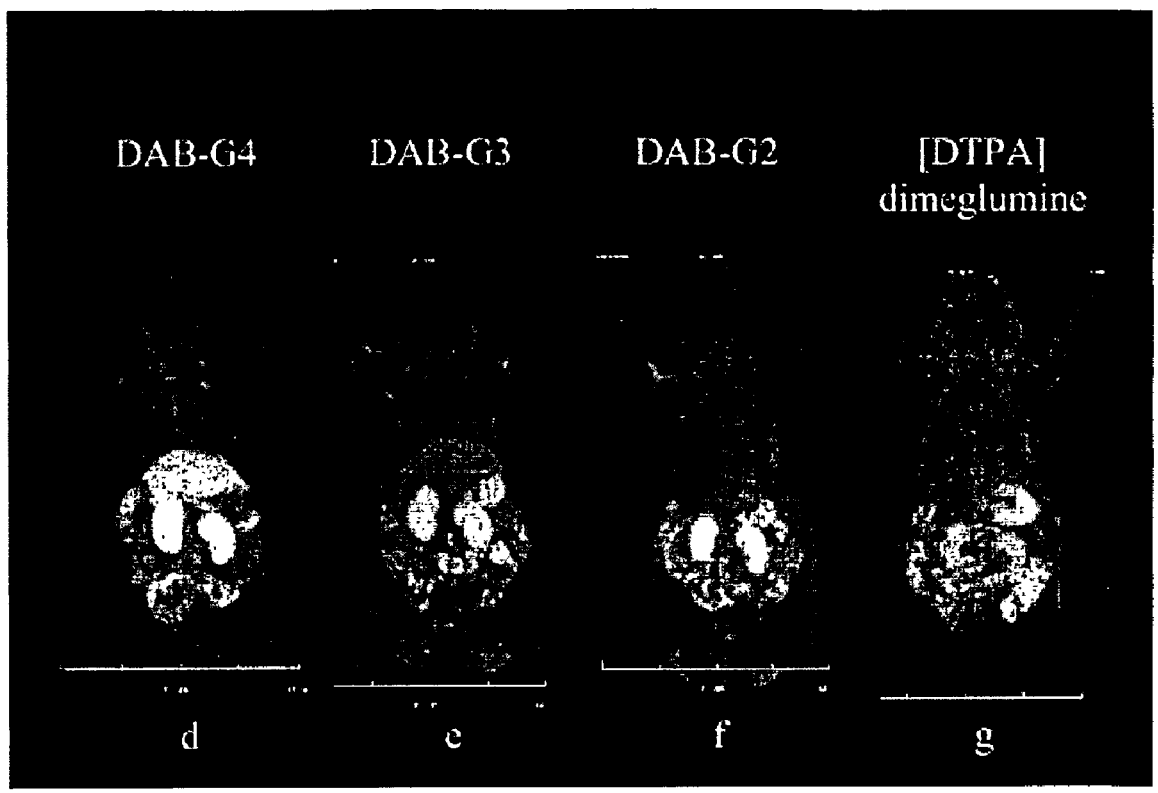
FIGS. 4 d-g

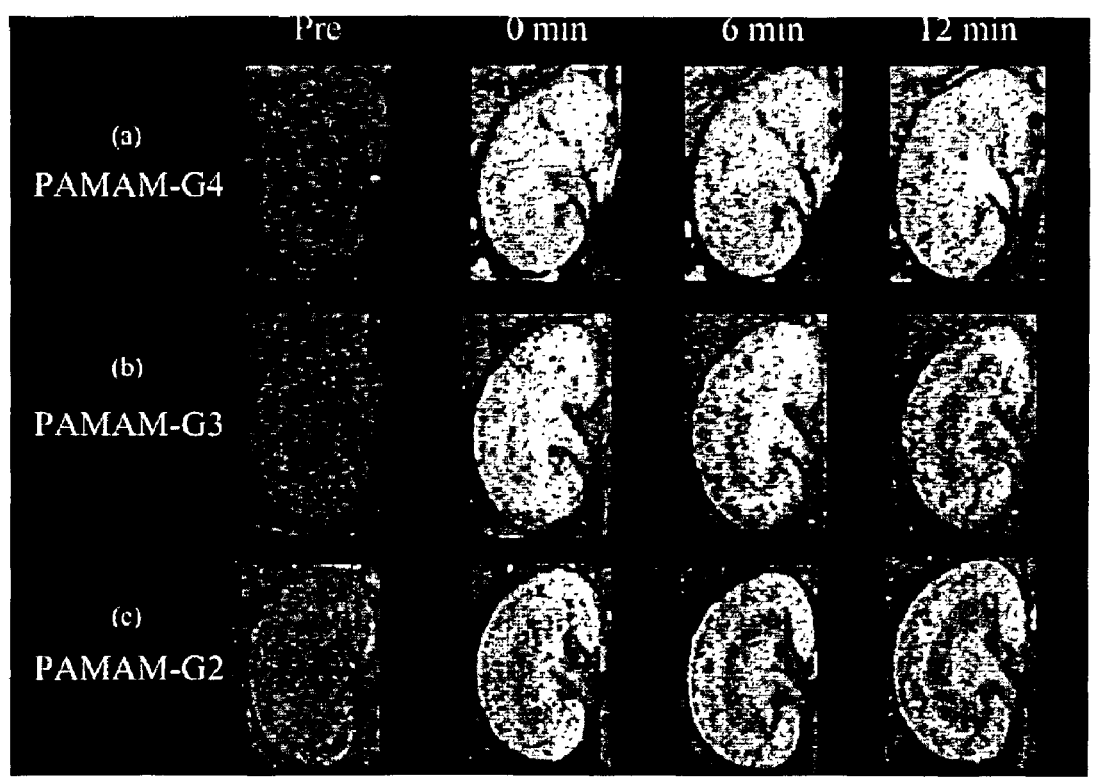
FIGS. 6 a-c

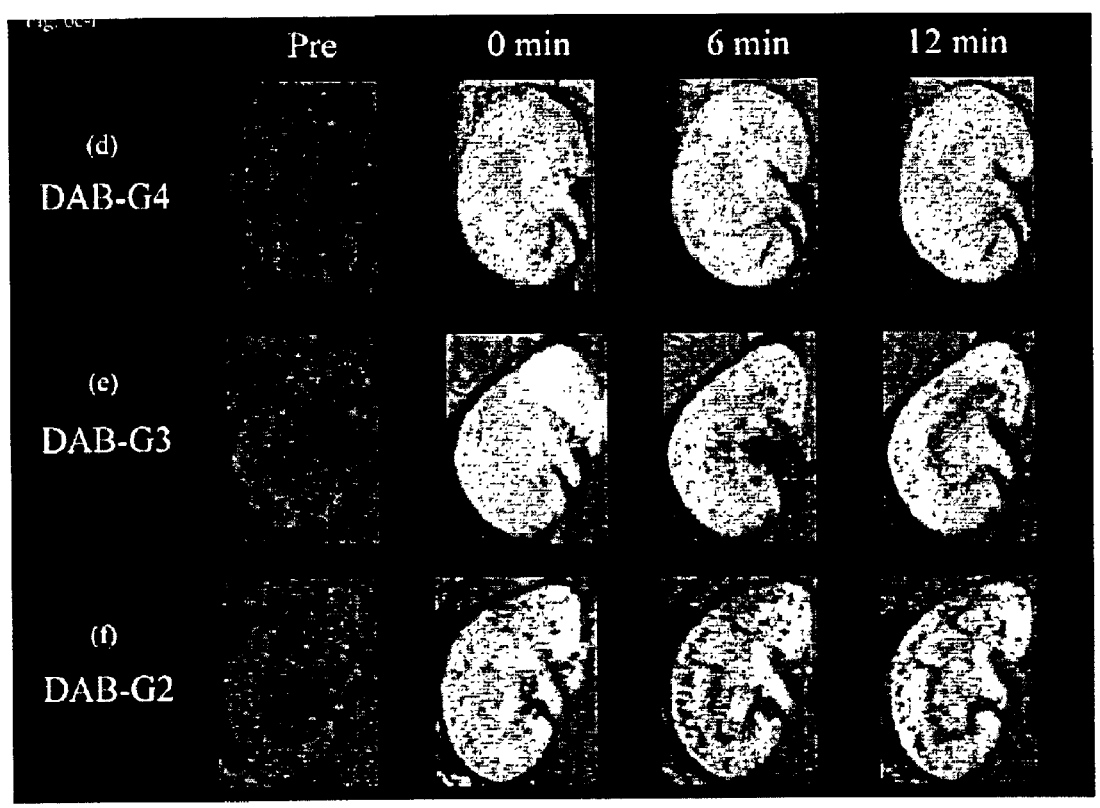
FIGS. 6 d-f

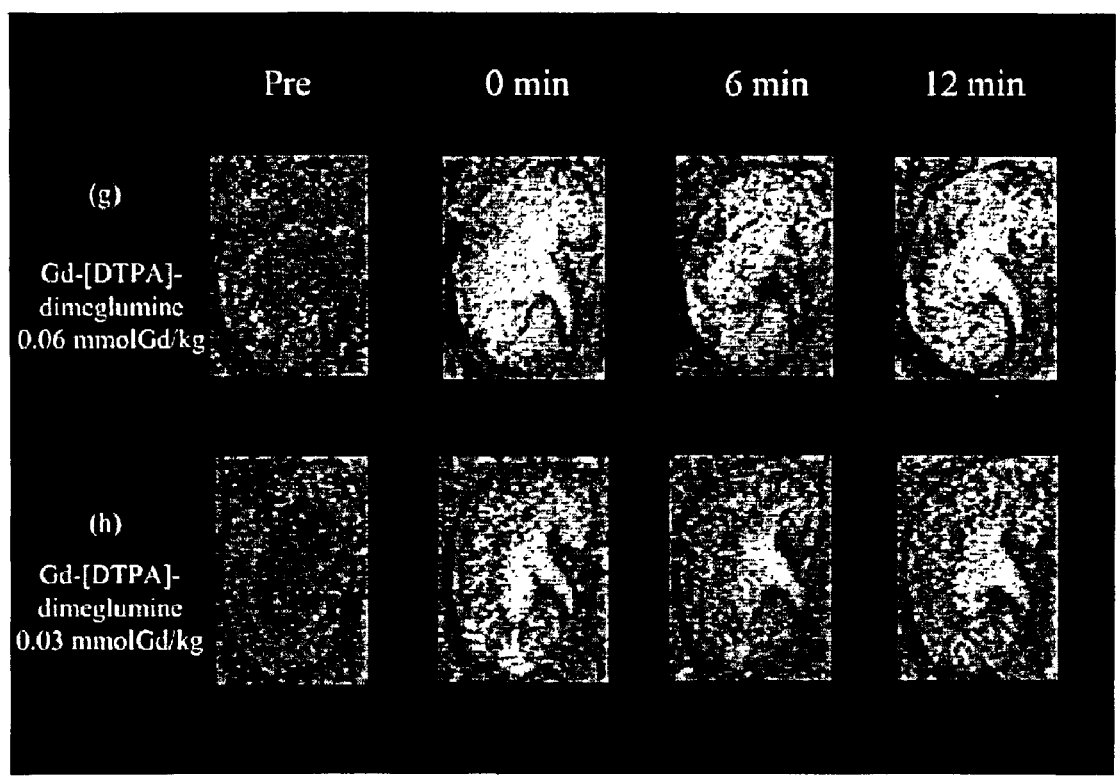
FIGS. 6 g-h

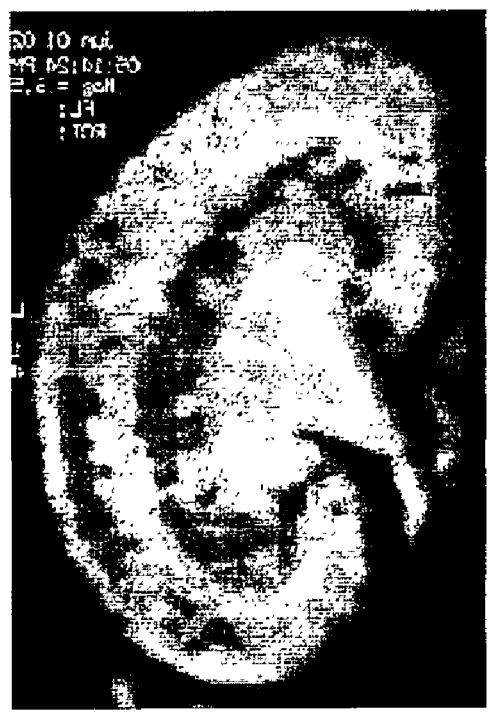 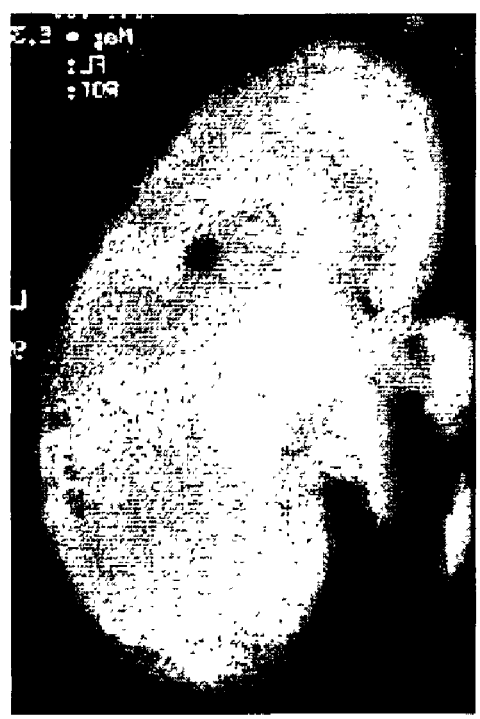
(a)          (b)
FIG. 7

METHODS FOR FUNCTIONAL KIDNEY IMAGING USING SMALL DENDRIMER CONTRAST AGENTS

FIELD

Methods of imaging kidney tissue are disclosed. More specifically, the disclosure relates to MRI methods that provide images that may be used to assess renal structure and function, and to detect renal injury.

BACKGROUND

MRI is a technique that allows whole body in vivo imaging in three dimensions at high resolution. In MRI, a static magnetic field is applied to the object of interest while simultaneously or subsequently applying pulses of radio frequency (RF) to change the distribution of the magnetic moments of protons in the object. The change in distribution of the magnetic moments of protons in the object from their equilibrium (normal) distribution to a non-equilibrium distribution and back to the normal distribution (via relaxation processes) constitute the MRI signal.

The longitudinal relaxation time, $T_1$, is defined as the time constant of the exponential recovery of proton spins to their equilibrium distribution along an applied magnetic field after a disturbance (e.g. a RF pulse). The transverse relaxation time, $T_2$, is the time constant that describes the exponential loss of magnetization in a plane transverse to the direction of the applied magnetic field, following a RF pulse that rotates the aligned magnetization into the transverse plane. Magnetic resonance (MR) contrast agents assist this return to a normal distribution by shortening $T_1$ and/or $T_2$ relaxation times.

Signal intensity in biological MRI depends largely on the local value of the longitudinal relaxation rate ($1/T_1$), and the transverse relaxation rate ($1/T_2$) of water protons. Contrast agents will increase $1/T_1$ and/or $1/T_2$, depending on the nature of the agent and the strength of the applied field. MRI pulse sequences that emphasize changes in $1/T_1$ are referred to as $T_1$-weighted and those that emphasize changes in $1/T_2$ are referred to as $T_2$-weighted. MR contrast agents that include gadolinium (III) ions increase both $1/T_1$ and $1/T_2$, and are primarily used with $T_1$-weighted imaging sequences, since the relative change in $1/T_1$ in tissue is typically much greater than the change in $1/T_2$. Iron particles, by contrast, provide larger relative changes in $1/T_2$, and are best visualized in a $T_2$-weighted image.

Advances in MRI have tended to favor $T_1$ agents such as gadolinium based contrast agents. Faster scans with higher resolution require more rapid RF pulsing, and can lead to loss of the MRI signal through saturation effects. $T_1$ agents relieve this saturation and restore signal intensity by stimulating relaxation of nuclear spins between RF pulses.

Because many paramagnetic metal ions, including gadolinium (III), are toxic, they are often administered in a sequestered form, for example, as metal chelates. However, metal chelates, because of their small size and relative hydrophillicity, tend to be cleared rapidly from blood, giving rise to limited cell penetration (but good tolerability). Conjugation of metal chelates to macromolecules to form macromolecular imaging agents is one approach to altering the pharmacological properties (e.g., blood retention, tissue perfusion, and excretion) and biophysical properties (e.g., relaxivity, which is defined as the increase in longitudinal or transverse relaxation rate per millimolar concentration of a contrast agent) of metal chelates. For example, high molecular weight macromolecular imaging agents tend to be retained in the vascular space by virtue of their size, and are useful for blood pool imaging in a technique called magnetic resonance angiography (MRA). Tissue specific accumulation and/or image enhancement are features that may be exhibited by macromolecular contrast agents due to their pharmacokinetic properties, but the mechanisms that lead to such by which this occurs are poorly understood outside of immunologically active contrast agents, such as antibodies conjugated to metal chelates.

Dendrimers are a class of highly branched, often spherical, macromolecular polymers that exhibit greater monodispersity (i.e. a smaller range of molecular weights, sizes, and shapes) than linear polymers of similar size. These three-dimensional oligomeric structures are prepared by reiterative reaction sequences starting from a core molecule that has multiple reactive groups. When monomer units, also having multiple reactive groups, are reacted with the core, the number of reactive groups comprising the outer bounds of the dendrimer increases. Successive layers of monomer molecules may be added to the surface of the dendrimer, with the number of branches and reactive groups on the surface increasing geometrically each time a layer is added. The number of layers of monomer molecules in a dendrimer may be referred to as the "generation" of the dendrimer. The total number of reactive functional groups on a dendrimer's outer surface ultimately depends on the number of reactive groups possessed by the core, the number of reactive groups possessed by the monomers that are used to grow the dendrimer, and the generation of the dendrimer.

The reactive functional groups that form the outer surface of a dendrimer may be conjugated to metal chelates, such as gadolinium (III) chelates, to provide macromolecular MRI contrast agents. Conjugation of multiple metal chelates to a dendrimer core to provide a dendrimer conjugate may provide a contrast agent exhibiting high relaxivities and altered pharmacokinetics relative to the metal chelates themselves. Unfortunately, selection of a dendrimer-based contrast agent that is suitable for imaging a particular tissue or tissue function (by virtue of a combination of distribution to the tissue and image enhancement of particular features of the tissue) is complicated by the current understanding of how molecules are processed and ultimately excreted (e.g. through the kidney and liver) from the body.

In particular, selection of dendrimeric agents for imaging of renal tissue is difficult in view of the complex way in which molecules are processed by renal tissue. For example, blood clearance and renal excretion of low-molecular weight molecules depends on glomerular filtration, which in turn relies on molecular shape and size (See, for example, Chang et al., "Permselectivity of the glomerular capillary wall to macromolecules," *Biophys. J*, 15: 887–906 (1975)). Molecular charge also affects renal filtration (See, for example, Guasch et al., "Charge selectivity of the glomerular filtration barrier in healthy and nephrotic humans," *J. Clin. Invest.*, 92: 2274–2282 (1993)). Once filtered, low-molecular weight molecules generally undergo endocytosis, another process that depends at least in part upon charge (See, for example, Kobayashi et al., "The pharmacokinetic characteristics of glycolated humanized anti-Tac Fabs are determined by their isoelectric points," *Cancer Res.*, 59: 422–430 (1999)). Furthermore, the relative hydrophobicity or hydrophillicity of a molecule has been shown to affect accumulation in the kidney. For example, a more hydrophobic DAB-Am-64-(1B4M)$_{64}$ dendrimer contrast agent has been shown to accumulate significantly more in the liver and less in the kidney than a relatively hydrophillic PAMAM- G4D-(1B4M)$_{64}$ contrast agent (Kobayashi et al., "Novel Liver Macromolecular MR Contrast Agent with a Polypropylenimine Diaminobutyl Dendrimer Core: Comparison to the Vascular MR Contrast Agent with the Polyamidoamine Dendrimer Core," *Magn. Res. Med.,* 46: 795–802 (2001)). The complicated dependence of renal processing on size, shape, charge and hydrophobicity (hydrophillicity) of a macromolecule makes it difficult to predict which agents will provide contrast for renal structure and function.

Further complicating the discovery of clinically suitable macromolecular MRI contrast agents is the danger that such agents will be retained for extended periods of time in the body, leading to increased potential toxicity from unstable Gd (III) chelates. For example, only 20 percent of the injected dose (% ID) of the PAMAM-G4D based contrast agent was excreted from mice during the first two days following administration (See, Sato et al., "Pharmacokinetics and enhancement patterns of macromolecular MR contrast agents with various sizes of polyamidoamine dendrimer cores," *Magn. Reson. Med.* 46: 1169–1173 (2001)). Efforts to increase the excretion rate of dendrimeric contrast agents can lead to altered image enhancement patterns. (See, for example, Kobayashi et. al., "Novel Intravascular Macromolecular MRI Contrast Agent With Generation-4 Polyamidoamine Dendrimer Core: Accelerated Renal Excretion with Coinjection of Lysine," *Magn. Res. Med.,* 46:457–464 (2001)).

SUMMARY

Contrast agents and methods useful for imaging the internal structure and function of the mammalian kidney are disclosed. Contrast agents prepared from small DAB and PAMAM dendrimers are disclosed to provide visualization of the proximal straight tubules of the kidney. In one disclosed method, an image-enhancing amount of contrast agent prepared from a DAB-G2D, DAB-G3D or PAMAM-G2D dendrimer is administered to a subject. Following administration, accumulation of the dendrimeric contrast agents in the proximal straight tubules may be monitored to assess kidney function. Abnormal function of the kidney may be inferred from differences in the way that renal tissue processes the contrast agent in comparison to normal renal tissue.

BRIEF DESCRIPTION OF THE DRAWINGS

FIG. 4 is a series of whole body 3D-micro-MR-images of mice injected with 0.03 mmol Gd/kg of dendrimer-1B4M-Gd conjugates or 0.1 mmol Gd/kg Gd-[DTPA]-dimeglumine [DAB-G4 (a), DAB-G3 (b), DAB-G2 (c), PAMAM-G4 (d), PAMAM-G3 (e), PAMAM-G2 (f), Gd-[DTPA]-dimeglumine (g)]. The images were obtained immediately after injection. Maximum intensity projections are shown. Similar images from all mice (n=4) in the same group injected with similar preparations were obtained.

FIG. 6 shows a series of coronal MRI images of the center of the right kidney obtained pre-injection and 0, 6, or 12 min post-injection of 0.03 mmol/kg of dendrimeric contrast agents DAB-G4 (a), DAB-G3 (b), DAB-G2 (c), PAMAM-G4 (d), PAMAM-G3 (e) and PAMAM-G2 (f), and images obtained pre-injection and 0, 6, or 12 min post-injection of 0.06 mmol/kg of Gd-[DTPA]-dimeglumine (g), and 0.03 mmol/kg of Gd-[DTPA]-dimeglumine (h).

FIG. 7 is a pair of MRI images, both taken 9 min post-injection of 0.03 mmol/kg PAMAM-G4 for a normal balb/c mouse (a) and for a COX-2 knockout mouse (b), showing the cortical thinning associated with chronic renal failure in the COX-2 knockout mouse.

DETAILED DESCRIPTION

In order to facilitate review of the various embodiments of the invention, the following explanations of specific abbreviations and terms are provided:

I. Abbreviations

MR—magnetic resonance

MRI—magnetic resonance imaging

DAB—diaminobutane

DTPA—diethylenetriaminepentaacetic acid

PAMAM—polyamidoamine

1B4M—2-(p-isothiocyanatobenzyl)-6-methyl-diethylenetriaminepentaacetic acid

DAB-G2—DAB-Am16-(Gd-1B4M)$_{16}$

DAB-G3—DAB-Am-32-(Gd-1B4M)$_{32}$

DAB-G4—DAB-Am-64-(Gd-1B4M)$_{64}$

PAMAM-G2—PAMAM-G2D-(Gd-1B4M)$_{16}$

PAMAM-G3—PAMAM-G3D-(Gd-1B4M)$_{32}$

PAMAM-G4—PAMAM-G4D-(Gd-1B4M)$_{64}$

II. Terms

Unless otherwise explained, all technical and scientific terms used herein have the same meaning as commonly understood by one of ordinary skill in the art to which this invention belongs. Definitions of common terms in magnetic resonance imaging may be found, for example, in Bushong, "Magnetic resonance imaging: physical and biological principles," Mosby, St. Louis Mo., 1996.

The singular terms "a," "an," and "the" include plural referents unless context clearly indicates otherwise. Similarly, the word "or" is intended to include "and" unless the context clearly indicates otherwise. The term "comprises" means "includes."

In one aspect, dendrimer conjugates useful for imaging kidney structure and function are disclosed. The term "dendrimer conjugate" refers to a dendrimer attached to one or more metal chelates. The term "metal chelate" refers to a complex of a metal ion and a group of atoms that serves to bind the metal ion. In some embodiments, a dendrimer conjugate may have fewer bound metal ions than it has groups of atoms capable of binding metal ions.

The term "bifunctional chelating agent" refers to a molecule that has at least two functional groups, one of which is a reactive group which can form a bond, such as a covalent bond, with another molecule, and one of which is a metal binding group. Bifunctional chelating agents may be reacted with dendrimers to provide dendrimer conjugates. Conjugation between a dendrimer and a metal chelate typically refers to formation of a covalent bond between the dendrimer and the metal chelate(s). However, in some instances ion-ion bonds, ion-dipole bonds, dipole-dipole bonds and hydrophobic interactions may be used to conjugate a dendrimer and a metal chelate.

Figure 1:
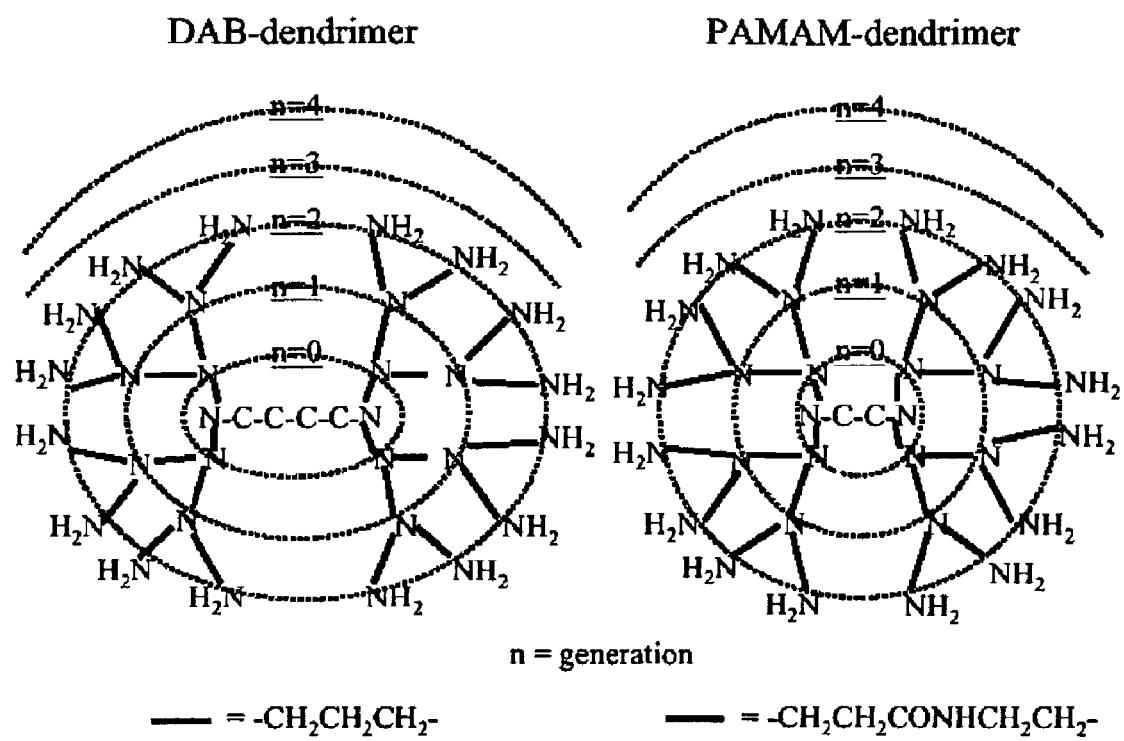
FIG. 1 is a diagram showing schematic structures of examples of the DAB and PAMAM types of dendrimers. The third and fourth generation dendrimer layers are not explicitly illustrated.

As used herein, the term "DAB dendrimer" refers to a dendrimer having a diaminobutane core and polyalkylenimine branches. In general, DAB dendrimers may have polyalkylenimine branches, such as polyethyleneimine, polypropylenimine and polybutyleneimine branches. The term "DAB-Am dendrimer" refers to a DAB dendrimer having polypropylenimine branches and one or more surface amino groups. The term "DAB-Am-X" refers to a DAB-Am dendrimer having X number of surface amino groups. For example, DAB-Am-4 denotes a diaminobutane-core dendrimer having polypropylenimine branches and 4 amino groups at its surface. Additional examples of DAB-Am-X dendrimers include DAB-Am-8, DAB-Am-16, DAB-Am-32 and DAB-Am-64. DAB-Am-X dendrimers having 4, 8, 16, 32 and 64 surface amine groups are also known, respectively, as N,N,N',N'-tetrakis(3-aminopropyl)-1,4-butanediaminepolypropylenimine tetraamine, 4,17-bis(3-aminopropyl)-8,13-bis[3-[bis(3-aminopropyl)-amino] propyl]-4,8,13,17-tetraazaeicosane-1,20-diamine, polypropylenimine hexadecaamine dendrimer [—CH$_2$CH$_2$N(CH$_2$)$_3$N[(CH$_2$)$_3$NH$_2$]$_2$]$_2$]$_2$], polypropylenimine dotriacontaamine dendrimer [—CH$_2$CH$_2$N(CH$_2$)$_3$N [(CH$_2$)$_3$NH$_2$]$_2$]$_2$]$_2$]$_2$], and polypropylene tetrahexacontaamine dendrimer [—CH$_2$CH$_2$N(CH$_2$)$_3$N[(CH$_2$)$_3$NH$_2$]$_2$]$_2$]$_2$]$_2$]$_2$]. As used herein, DAB-Am-X dendrimers having 4, 8, 16, 32 and 64 surface amine groups are also referred to, respectively, as DAB-G1D, DAB-G1D, DAB-G2D, DAB-G3D and DAB-G4D dendrimers, where the numbers refer to the generation of the dendrimer. A variety of DAB-Am-X dendrimers, including the specific examples listed immediately above, are available from Aldrich (Milwaukee, Wis.). Note, however, that Aldrich refers to these specific DAB-Am-X dendrimers as generations 1 through 5. In order to permit a comparison between generations of DAB-Am dendrimers and PAMAM dendrimers (discussed below) having equal numbers of amine groups on their surfaces, the generation numbers used by Aldrich may be reduced by one. The two types of dendrimers are compared in FIG. 1, which shows a schematic representation of the structures and generation numbers of some examples of both DAB-Am and PAMAM dendrimers.

DAB-Am dendrimers also may be synthesized according to the methods disclosed in Womer, and Mulhaupt, *Angew Chem., Int. Ed. Engl,* 32: 1306–1308, 1993. De Brabander-van den Berg and Meijer (*Angew. Chem., Int. Ed. Engl.,* 32:1308, 1993) also describe similar methods. Polypropylenimine dendrimers having other initiator cores, such as ammonia, ethylenediamine, propylenediamine, and other polyamines such as tris-aminoethylamine, cyclene, hexaazacyclooctadecane, 1,5 diaminopentane, ethylenetriamine, triethylenetetramine, 1,4,8,11-tetraazaundecane, 1,5,8,12-tetraazaundodecane, and 1,5,9, 13-tetraazatridecane. Typically, the surface of the polypropylenimine dendrimer will have one or more amino groups. However, some or all of the surface amino groups may be modified, for example, to provide other reactive groups or charged, hydrophilic, and/or hydrophobic groups such as carboxylate, hydroxyl and alkyl groups on the surface. Similar schemes may be used to synthesize polybutylenimine and higher polyalkylenimine dendrimers.

The term "PAMAM dendrimer" refers to a dendrimer having polyamidoamine branches. Like the DAB dendrimers discussed above, a variety of PAMAM dendrimers are commercially available from Aldrich (Milwaukee, Wis.). In particular, generation 1.0, 2.0, 3.0 and 4.0 PAMAM dendrimers, having ethylenediamine cores and, respectively, 8, 16, 32 and 64 surface amine groups, are commercially available. As used herein, these particular dendrimers are referred to, respectively, as PAMAM-G1D, PAMAM-G2D, PAMAM-G3D and PAMAM-G4D dendrimers. PAMAM dendrimers, also may be synthesized from a variety of core molecules (e.g., those described above for DAB dendrimers) according to the methods disclosed in U.S. Pat. No. 5,338, 532. Dendrimers having other surface groups, such as carboxylate and hydroxyl, also are available commercially (Aldrich, Milwaukee, Wis.) or may be provided by the methods disclosed in U.S. Pat. No. 5,338,532.

The metal chelate in a dendrimer conjugate is a complex of a metal ion and a metal binding group (a group of atoms that serves to bind or chelate the metal ion). Examples of metal binding groups include natural and synthetic amines, porphyrins, aminocarboxylic acids, iminocarboxylic acids, ethers, thiols, phenols, glycols and alcohols, polyamines, polyaminocarboxylic acids, polyiminocarboxylic acids, aminopolycarboxylic acids, iminopolycarboxylic acids, nitrilocarboxylic acids, dinitrilopolycarboxlic acids, polynitrilopolycarboxylic acids, ethylenediaminetetracetates, diethylenetriaminepenta or tetraacetates, polyethers, polythiols, cryptands, polyetherphenolates, polyetherthiols, ethers of thioglycols or alcohols, polyaminephenols, all either acyclic, macrocyclic, cyclic, macrobicyclic or polycyclic, or other similar ligands which produce stable metal chelates or cryprates (including sepulchrates, sacrophagines, and crown ethers).

Specific examples of metal chelating groups include diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N (2-aminoethyl)amide and DOTA-N-(2-aminophenethyl) amide, BOPTA, HP-DO3A, DO3MA, and various derivatives and combinations thereof. Other examples are provided in Caravan et al., *Chem. Rev.,* 99: 2293–2352, 1999. Since it is advantageous for in vivo imaging to select a metal chelating group capable of tightly binding a metal ion, a high stability constant for the metal chelate is desired.

Metals ions of the metal chelates may be paramagnetic ions if the imaging agent is to be used as a MRI contrast agent. Suitable ions include ions of metals having atomic numbers of 22–29 (inclusive), 42, 44 and 58–70 (inclusive) and combinations thereof. In particular embodiments, the metal ions have an oxidation state of 2 or 3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III), and combinations thereof. Particular examples of useful ions for MRI include the paramagnetic ions of gadolinium, dysprosium, cobalt, manganese, and iron. In a particular disclosed embodiment, the metal ion is a Gd (III) ion.

If the macromolecular imaging agent is to be used as an X-ray contrast agent, the metal ion may be selected from the ions of W, Bi, Hg, Os, Pb, Zr, lanthanides, and combinations thereof. If a combined MRI/X-ray contrast agent is desired, the metal ion may be selected from the paramagnetic lanthanide ions. If a radiographic imaging agent is desired, the metal may be radioactive, such as the radioactive isotopes of In, Tc, Y, Re, Pb, Cu, Ga, Sm, Fe, or Co.

The unique localization properties of the disclosed dendrimer conjugates also make it possible to use them for delivery of therapeutic radiation to particular tissues and tissue structures. Examples of metal ions useful for therapy include ions of the radioactive isotopes of Pb, Bi and Y.

Bifunctional chelating agents may be used to form a dendrimer conjugate. A bifunctional chelating agent is a molecule capable of forming a bond with another molecule, such as a dendrimer, and also capable of forming a metal chelate by binding a metal ion. Appropriate bifunctional chelating agents therefore include a reactive group and a metal chelating group, such as the metal chelating groups described above.

The reactive group of a bifunctional chelating agent is a group of atoms that that will undergo a reaction with a surface group of a dendrimer to form a bond, such as a covalent bond. Examples of reactive groups include carboxylic acid groups, diazotiazable amine groups, N-hydroxysuccinimidyl, esters, aldehydes, ketones, anhydrides, mixed anhydrides, acyl halides, maleimides, hydrazines, benzimidates, nitrenes, isothiocyanates, azides, sulfonamides, bromoacetamides, iodocetamides, carbodiimides, sulfonylchlorides, hydroxides, thioglycols, or any reactive group known in the art as useful for forming conjugates. If the dendrimer is a DAB-Am dendrimer, the reactive group may be a functional group capable of undergoing reaction an amino group of the DAB-Am dendrimer.

Specific examples of bifunctional chelating agents include bifunctional diethylenetriaminepentaacetic acid (DTPA) derivatives such as those disclosed in U.S. Pat. No. 5,434,287 to Gansow et al. Other examples include polysubstituted diethylenetriaminepentaacetic acid chelates such as those described by Gansow et al. in U.S. Pat. No. 5,246,692. Bifunctional chelating agents comprising 1,4,7,10-Tetraazacyclododecane-N,N',N",N'"-tetraacetic acid (DOTA) and its derivatives are also useful. Examples of bifunctional DOTA derivatives are provided in U.S. Pat. No. 5,428,154 to Gansow et al. and references therein. A particular example of a bifunctional imaging agent is 2-(p-isothiocyanatobenzyl)-6-methyl-diethylenetriaminepentaacetic acid (1B4M).

Macromolecular imaging agents may be prepared by reacting a surface group of a dendrimer with the reactive group of a bifunctional chelating agent and then reacting the metal chelating group of the bifunctional chelating agent with a metal ion. Alternatively, a metal ion is reacted with the metal chelating group of the bifunctional chelating agent prior to reacting the reactive group of the bifunctional chelating agent with a surface groups of the dendrimer. Metal chelation is typically carried out in solution, and desirably avoids the use of strong acids or bases. In particular embodiments, a dendrimer selected from the group consisting of DAB-G2D, DAB-G3D, DAB-G4D, PAMAM-G2D, PAMAM-G3D and PAMAM G4D is reacted with 1B4M and gadolinium ions (in either order discussed above) to provide dendrimer conjugates suitable for kidney imaging.

Thus, in one aspect, dendrimer conjugates suitable for kidney imaging are provided. Particular examples include DAB-G2 [DAB-Am16-(Gd-1B4M)$_{16}$], DAB-G3 [DAB-Am-32-(Gd-1B4M)$_{32}$], DAB-G4 [DAB-Am-64-(Gd-1B4M)$_{64}$], PAMAM-G2 [PAMAM-G2D-(Gd-1B4M)$_{16}$], PAMAM-G3 [PAMAM-G3D-(Gd-1B4M)$_{32}$] and PAMAM-G4 [PAMAM-G4D-(Gd-1B4M)$_{64}$]. Table 1 compares some properties of these conjugates and the simple gadolinium chelate, Gd-DTPA-dimeglumine.

TABLE 1

Comparison of Example Contrast Agents.

| Name used herein. | MW (kD) | Gd atoms | Core MW (kD) | Commercial name (of dendrimer core where applicable) |
|---|---|---|---|---|
| PAMAM-G4 | 59 | 64 | 14.2 | PAMAM G4 |
| PAMAM-G3 | 29 | 32 | 6.9 | PAMAM G3 |
| PAMAM-G2 | 14 | 16 | 3.5 | PAMAM G2 |
| DAB-G4 | 51 | 64 | 7.1 | DAB-Am-64 |
| DAB-G3 | 25 | 32 | 3.5 | DAB-Am-32 |
| DAB-G2 | 12 | 16 | 1.7 | DAB-Am-16 |
| Gd-DTPA-dimeglumine | 0.8 | 1 | N/A | Magnevist |

In particular embodiments, dendrimer conjugates are disclosed where the conjugates comprise a dendrimer selected from the group consisting of DAB-G2D, DAB-G3D and PAMAM-G2D and a gadolinium (III) chelate of 1B4M. In more particular embodiments, the dendrimer is selected from the group consisting of DAB-G2D and DAB-G3D.

In another aspect, methods are disclosed for imaging kidney tissue. These methods include administering to a subject an image-enhancing amount of a dendrimer conjugate, the dendrimer conjugate comprising a dendrimer selected from the group consisting of DAB-G2D, DAB-G3D, DAB-G4D, PAMAM-G2D, PAMAM-G3D, PAMAM-G4D and combinations thereof, and a metal chelate. Once administered, a difference in a magnetic resonance signal intensity of at least a portion of the kidney is detected. Differences in intensity may be used to detect structural and/or functional features of the kidney. For example, a portion of the kidney comprising the proximal straight tubules or the pelvis of the kidney may be imaged, and the image(s) used to detect whether the kidney is functioning to process the dendrimer conjugate in a manner characteristic of normal kidney tissue. Images characteristic of normal kidney function may be obtained from a subject that has no clinical indications of renal dysfunction (e.g. elevated BUN levels or creatine levels), and such images may be compared with images obtained from subjects that do not exhibit clinical indications of renal dysfunction. In yet other embodiments, cortical thinning associated with chronic renal failure may be detected by measuring the thickness of the cortex and/or outer medulla in an image obtained according to the disclosed methods. Such images may be useful for differentiating acute from chronic renal failure, and may also be used to detect renal cysts associated with chronic renal failure.

In particular embodiments of the disclosed methods, detecting a difference in a magnetic resonance signal intensity of at least a portion of the kidney comprises detecting a difference in a T1-weigthed signal at a position corresponding to the proximal straight tubules of the kidney, for example, the outer stripe of the outer medulla of the kidney. Alternatively, detecting a difference in a magnetic resonance signal intensity of at least a portion of the kidney comprises detecting a signal associated with the appearance of urine in the pelvis of the kidney as the dendrimer conjugate is excreted. For example, an increase in the signal intensity in the region of the kidney pelvis may be followed over time and used to assess kidney function.

In other embodiments, the methods also include comparing the difference in magnetic resonance signal intensity detected for the subject to a difference in signal intensity detected in a second subject to determine whether the kidneys of the subject and the second subject are similar in structure or function. For example, a second subject exhibiting acute renal failure may be used for comparison to detect whether the subject also exhibits a MRI signal indicative of acute renal failure.

In some embodiments, the methods include administering a dendrimer conjugate to a subject where the metal chelate of the dendrimer conjugate is selected from the group consisting of metal chelates of diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N(2-aminoethyl)amide and DOTA-N-(2-aminophenethyl)amide, BOPTA, HP-DO3A, DO3MA, and derivatives and combinations thereof. The metal chelate may comprise an ion of a metal selected from the group consisting of the metals having atomic numbers of 22–29, 42, 44 and 58–70 and combinations thereof. In particular embodiments, the ion is selected from the group consisting of chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), ytterbium (III) and combinations thereof. In particular embodiments, the dendrimer conjugate is a 1B4M conjugate and is selected from the group consisting of DAB-G2, DAB-G3, DAB-G4, PAMAM-G2, PAMAM-G3, PAMAM-G4 and combinations thereof.

When a dendrimer conjugate is used as an imaging agent for imaging the kidney of a subject (i.e. a mammal such as a mouse or a human), the conjugate is administered in an image enhancing amount [i.e. an amount sufficient to produce detectable (e.g. visually detectable or electronically detectable) differences in the image of the kidney at some time following administration]. For MRI, such differences may be detected in either a $T_1$- or $T_2$-weighted image taken at some time after the imaging agent is administered. The differences may be due to either an increase or a decrease in the intensity of the kidney or a portion thereof, relative to surrounding tissue in comparison to an image obtained before administration of the agent. In one embodiment, dendrimer conjugates for MRI are administered in dosages that are ¼ to ⅓ the dosages required for simple chelates such as Gd-DOTA and Gd-DPTA. In particular embodiments, a detectable difference in kidney MRI image intensity may be provided by administering between about 0.001 mmol Gd/kg and about 0.10 mmol Gd/kg, for example, administering between about 0.003 mmol Gd/kg and about 0.03 mmol Gd/kg intravenously or parenterally. Imaging may begin immediately or anywhere from about 1 min to about 2 hrs after administration, such as between about 3 minutes and 60 minutes after administration.

All publications, patent applications, patents, and other references mentioned herein are incorporated by reference in their entirety. In case of conflict, the present specification, including explanations of terms, will control. In addition, the materials, methods, and examples are illustrative only and not intended to be limiting. Various embodiments are illustrated by the following non-limiting Examples.

EXAMPLE 1

Preparation of Dendrimer Conjugates

Dendrimers were concentrated to 10 mg/ml, and diafiltrated against 0.1 M sodium phosphate buffer at pH 9 and reacted at 40° C. with a 16, 32, or 64-fold molar, excess of 2-(p-isothiocyanatobenzyl)-6-methyl-diethylenetriamine-pentaacetic acid (1B4M) for the generation-2, -3, and -4 PAMAM and DAB dendrimers, respectively. The reaction solutions were maintained at pH 9 with 1 M NaOH over the reaction time of 48 hr. Additional 1B4M equal to the initial amount was added as a solid after 24 hours to each reaction. The resulting preparation was purified by diafiltration using a Centricon 30 (Amicon Co., Beverly, Mass.) for the generation-4 dendrimers and a Centricon 10 (Amicon Co.) for generation-2 and -3 dendrimers. Over 98% of the amine groups on the dendrimers reacted with the 1B4M as determined by a $^{153}$Gd labeling assay of the products.

Radioactive dendrimer conjugates used for biodistribution studies were prepared as follows. $^{153}$GdCl$_3$ containing no other stable isotope of Gd (III) was purchased from NEN DuPont (Boston, Mass.). Approximately 1,500 $\mu$g of each dendrimer (containing 2 $\mu$mol of 1B4M) was reacted with 1.11 MBq (30 $\mu$Ci) of $^{153}$Gd citrate (46 pmol) in 0.3 M citrate buffer at pH 5 for 30 min at room temperature. The preparation was then mixed with a 3-fold molar excess of non-radiolabeled Gd(III) citrate (6 $\mu$mol) to conjugate 1B4M to fully saturate the chelating groups with Gd(III). This reaction was incubated for 30 min before the addition of ethylenediaminetetraacetic acid (EDTA) and subsequent column purification. To remove any non-incorporated free metal, 10 $\mu$l of 0.5 M EDTA (Sigma, St. Louis, Mo.) was added to minimized formation of Gd(OH)$_3$ precipitate. The product was purified using a PD-10 column (Pharmacia, Uppsala, Sweden), eluting with PBS, (pH 7.4). The radio-purity of each preparation was analyzed by size-exclusion HPLC using a TSK G3000SW column (TosoHaas, Philadelphia, Pa.; 0.1 M PBS; 0.01 M KCl; pH 7.4; 1 ml/min). DTPA (Sigma) was also labeled with $^{153}$Gd in 0.3-M citrate buffer for 30 min at room temperature. The radiolabeling yields of all preparations ranged from 47% to 55%. The radio-purity of all preparations analyzed by size-exclusion HPLC was greater than 97%.

Non-radioactive gadolinium dendrimer conjugates where prepared as follows. The dendrimer-1B4M conjugates (containing 4 $\mu$mol of 1B4M) were mixed with 6.5 $\mu$mol of Gd (III) citrate (Sigma) in 0.3 M citrate buffer for 2 hr at 40° C. The excess Gd (III) in each preparation was removed by diafiltration using a Centricon 30 (Amicon Co., Beverly, Mass.) for generation-4 dendrimers and a Centricon 10 (Amicon Co.) for generation-2 and -3 dendrimers, while simultaneously changing the buffer to 0.05 M PBS. Briefly, the conjugated samples were applied on Centricon 30 or 10 and centrifuged at ~3,000 g for 45 min. Thereafter 2 ml of 0.05 M PBS was added to 20 $\mu$l of the concentrated samples. The samples were again centrifuged at ~3,000 g for 45 min. The purified samples were diluted to 1 ml with 0.05 M PBS and 100 $\mu$l of this final solution was used per mouse. A replacement assay using $^{153}$Gd showed that the number of 1B4M chelators of the dendrimer-1B4M conjugates chelating Gd(III) atoms ranged from 77% to 87%. In brief, approximately 500,000 counts per minute (9.3 kBq [0.25 $\mu$Ci]) of $^{153}$Gd citrate (0.38 pmol) were added with 0.1 $\mu$mol of non-radioactive Gd(III) to 5 μl of the injected samples and incubated in 0.5 M citrate buffer for 2 hr at 40° C. After this time, the bound and unbound fractions were separated as described above using a PD-10 column (Pharmacia).

The purified contrast agents were analyzed by size-exclusion HPLC using a TSK G3000SW column (TosoHaas, Philadelphia, Pa.; 0.1 M PBS; 0.01 M KCl; pH 7.4; 1 ml/min) using a UV detector to detect any free 1B4M chelate at 280 nm absorbance.

EXAMPLE 2

Biodistribution and Whole Body Retention of $^{153}$Gd-Labeled Dendrimer-1B4M-Gd Conjugates Seven groups of nude mice (n=4 in each group) were injected with 37 kBq (1 μCi)/200 μl of $^{153}$Gd-labeled dendrimer-1B4M-Gd conjugates or $^{153}$Gd-DTPA. The injected samples were added to non-radioactive preparations and the total gadolinium dose was adjusted to 0.02 mmol Gd/kg, 20% of the dose of Gd-[DTPA]-dimeglumine routinely used clinically. The mice were sacrificed 15 min after the injection of the $^{153}$Gd-labeled preparations and biodistribution studies were performed. The data were expressed as the percentage of the injected dose per gram (% ID/g) of tissue. The carcasses of the mice were also counted to calculate the whole body retention (% ID).

Figure 2A:
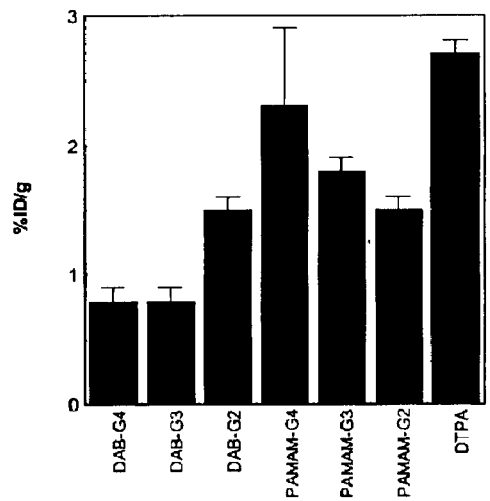
FIG. 2 is a series of bar graphs showing the retention of $^{153}$Gd-labeled dendrimer-1B4M-Gd conjugates and $^{153}$Gd-DTPA in the blood (a), liver (b) and kidney (c) in normal nude mice (n=4) at 15 min after injection. The values are expressed as the mean percentages of the injected dose per gram of normal tissues and standard deviation.
Figure 2B:
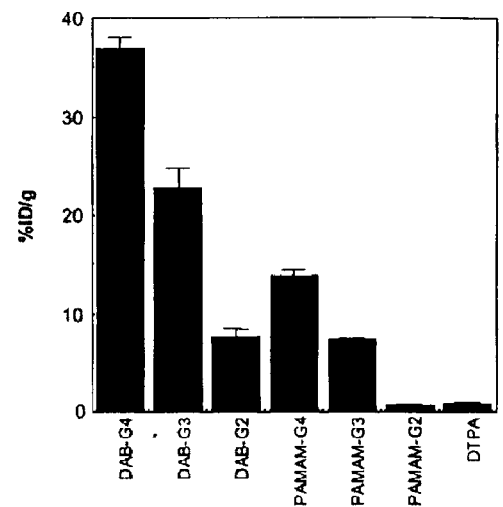
Figure 2C:
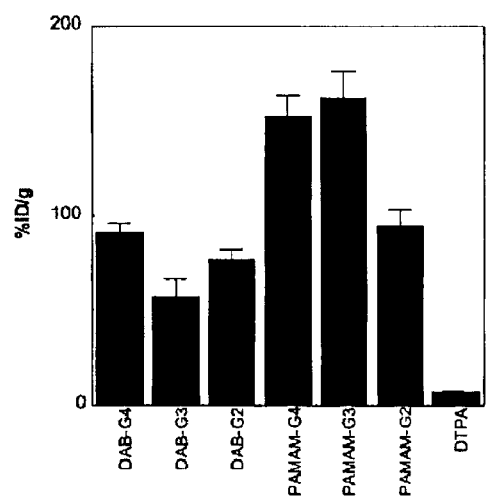
Figure 3:
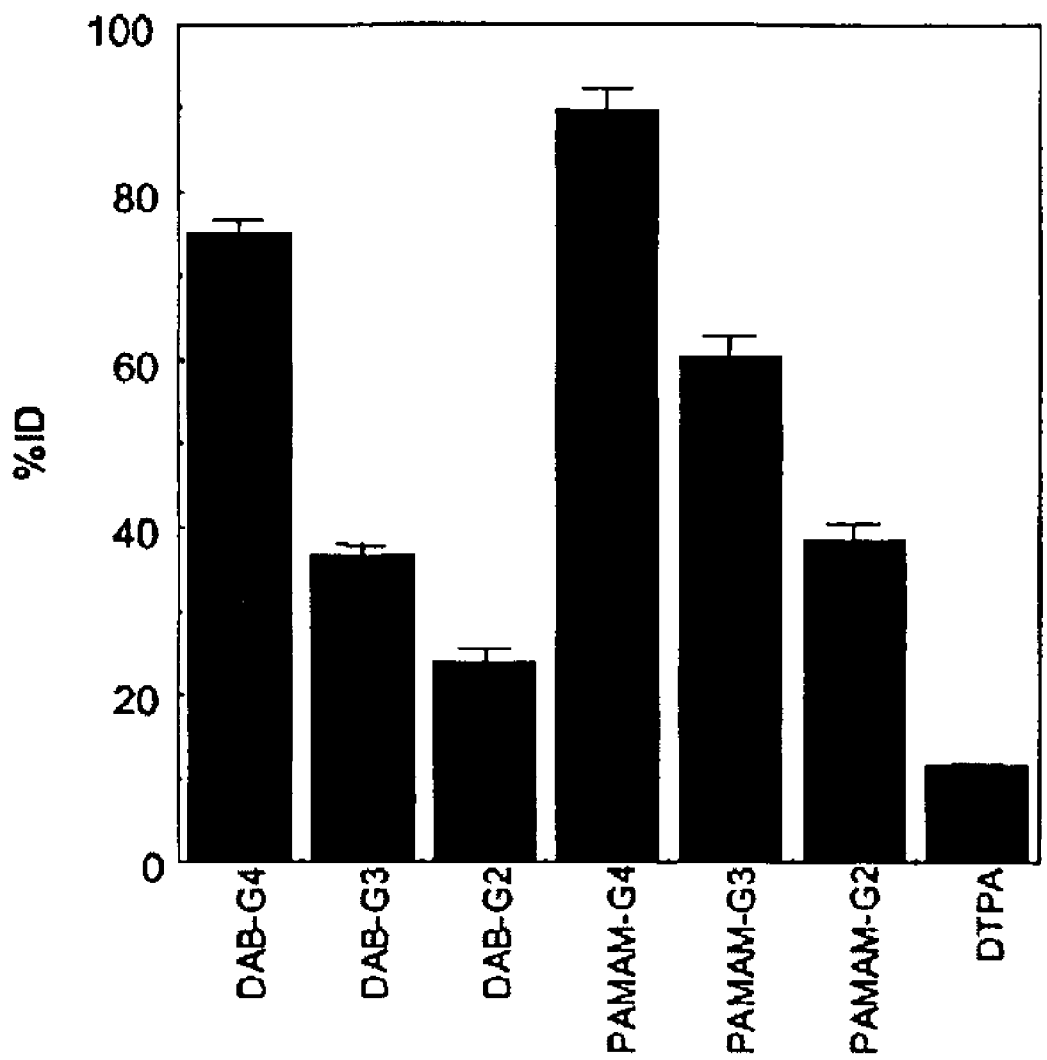
FIG. 3 is a bar graph showing the whole body retention of $^{153}$Gd-labeled dendrimer-1B4M-Gd conjugates or $^{153}$Gd-DTPA in a normal nude mice (n=4) at 15 min after injection. The values are expressed as the mean percentages of the injected dose of mice and standard deviation.

The $^{153}$Gd-labeled DAB-based agents accumulated significantly greater in the liver (FIG. 2b) and less in the kidney (FIG. 2c) than $^{153}$Gd-labeled PAMAM-based agents (p<0.001). The amount of the $^{153}$Gd-labeled DAB-based agents remaining in the blood (FIG. 2a) increased as the molecular weight increased (1.5±0.2, 0.8±0.1, 0.7±0.1, and % ID/g for the DAB-G2D, -G3D, and -G4D, respectively). In contrast, the amount of $^{153}$Gd-labeled PAMAM-based agents remaining in blood decreased as the molecular weight increased (1.5±0.1, 1.8±0.1, and 2.3±0.4 % ID/g for PAMAM-G2D, -G3D, and -G4D, respectively) (FIG. 2c). However, all conjugates were cleared from blood circulation more rapidly than Gd-DTPA (2.7±0.1% ID/g). The whole body retention of the DAB-based agents was less than that of the PAMAM-based agents of the same dendrimer generation (See, FIG. 3). Greater than 60% ID of the DAB-G3D, DAB-G2D, and PAMAM-G2D based contrast agents were cleared from the body within 15 min after injection.

EXAMPLE 3

Contrast-Enhanced Dynamic 3D-Micro-MRI of Mice

To evaluate the whole body pharmacokinetics of the contrast agents, seven groups of 8-week-old female nude mice (n=4 in each group) (NCI, Frederick, Md.) were used to obtain contrast-enhanced dynamic 3D-micro-MR images. Briefly, either 0.03 mmol Gd/kg (30% of clinical dose) of dendrimer-1B4M-Gd conjugates or 0.1 mmol Gd/kg of Gd-[DTPA]-dimeglumine (Magnevist, Schering, Berlin, Germany) were intravenously injected into the left tail vein. All images were obtained using the high-resolution wrist coil (GE) with a custom mouse holder using a clinical-grade 1.5-tesla superconductive magnet unit (Signa LX, General Electric Medical System, Milwaukee, Wis.). The mice were anesthetized with 1.15 mg of sodium pentobarbital (Dainabot, Osaka, Japan) and placed in the center of the coils. The fast spoiled gradient echo technique (FSPGR; TR/TE 19.4/4.2; flip angle 60°; scan time 1'40"; phase encoding steps 256×256; 3 number of excitations; slab thickness 12) with chemical fat-suppression technique and serial 3D data acquisition was used to acquire images every 2 min from 0 (immediately after injection) to 14 min after injection of the contrast agents for all mice studies. The coronal images for dynamic MRI were reconstructed with 2-mm section thickness without gap reconstruction. In addition, slice data was processed into 3D images with the maximum intensity protection (MIP) method (Advantage Windows, General Electric Medical System).

To evaluate visualization of detailed renal anatomy, serial dynamic MR images of the kidneys of mice (n=3 in each group) were obtained following injection of either 0.03 mmol Gd/kg (30% of clinical dose) of either a dendrimer-1B4M-Gd conjugate or 0.03 mmol Gd/kg or 0.06 mmol Gd/kg double dose (30 or 60% of clinical dose) of Gd-[DTPA]-dimeglumine (Schering) using a 1.5-tesla superconductive magnet unit (Signa LX), and an custom 1-inch bird-cage surface coil. The mice were anesthetized with 1.15 mg of sodium pentobarbital (Dainabot, Osaka, Japan) and placed in the center of the coils. The fast spoiled gradient echo technique (efgre3d; TR/TE 31.2/8; TI 71; flip angle 30°; scan time 3'07"; phase encoding steps 512×256; 2 number of excitations; slab thickness 16) with fat-suppression technique and serial 3D data acquisition was used to acquire images every 3.1 min from 0 (immediately after injection) to 12 min after injection of the contrast agents for all mice studied. The coronal images were reconstructed with 0.6-mm thick sections with a 0.3-mm overlap reconstruction. The field of view was 6×3 cm and the size of the matrix was 512×256. The reproducibility of the experiments (two mice in each group) was confirmed by repeating the experiments under the same conditions using a different 1.5-tesla superconductive MRI instrument (Signa Horizon, GE).

Whole body, maximum-intensity projection 3D-micro-MR images obtained immediately following intravenous injection of 0.03 mmol Gd/kg of dendrimers are shown in FIG. 4. Brighter liver images were obtained with DAB-based agents (FIGS. 4d–f) than PAMAM-based agents (FIGS. 4a–c) or Gd-[DTPA]-dimeglumine (FIG. 4g). All of the agents except Gd-[DTPA]-dimeglumine provided bright kidney images.

Figure 5A:
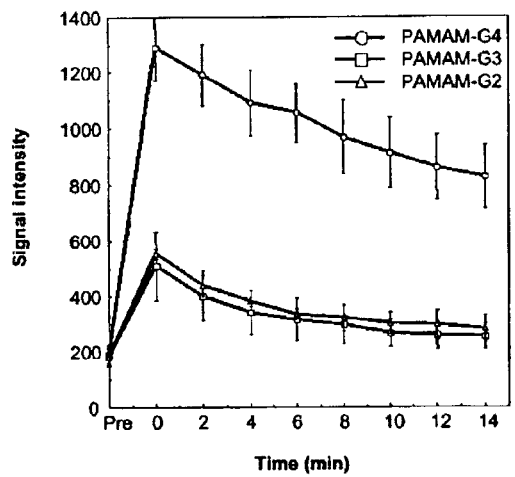
FIG. 5 is a series of graphs showing the MR signal intensity of the blood in the left ventricle of the heart (a, b), the kidney (c, d) and the liver (e, f), obtained from the contrast-enhanced dynamic MRI of mice with 0.03 mmol/kg of dendrimer-1B4M-Gd conjugates (as indicated) or 0.1 mmol Gd/kg Gd-[DTPA]-dimeglumine (DTPA). A single region of interest was set in each organ of each mouse (n=4). The data are expressed as the mean signal intensity and standard deviation.
Figure 5B:
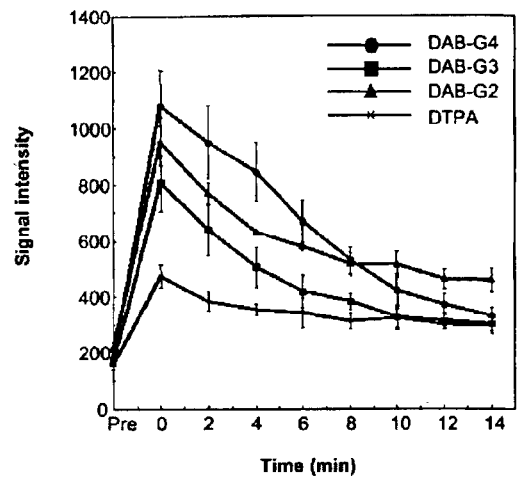
Figure 5C:
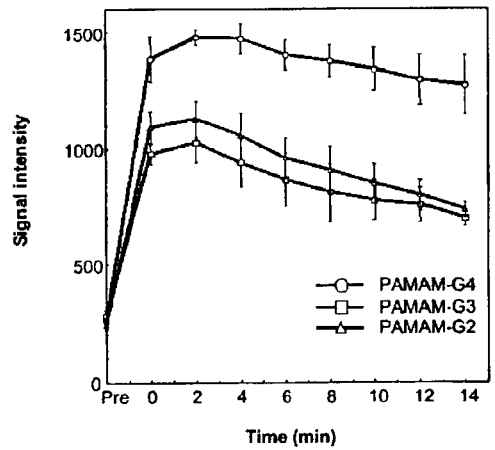
Figure 5D:
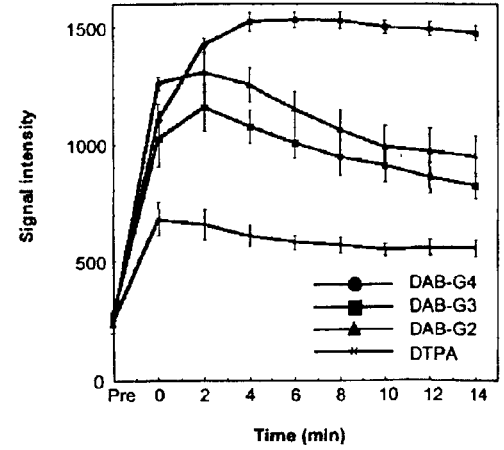
Figure 5E:
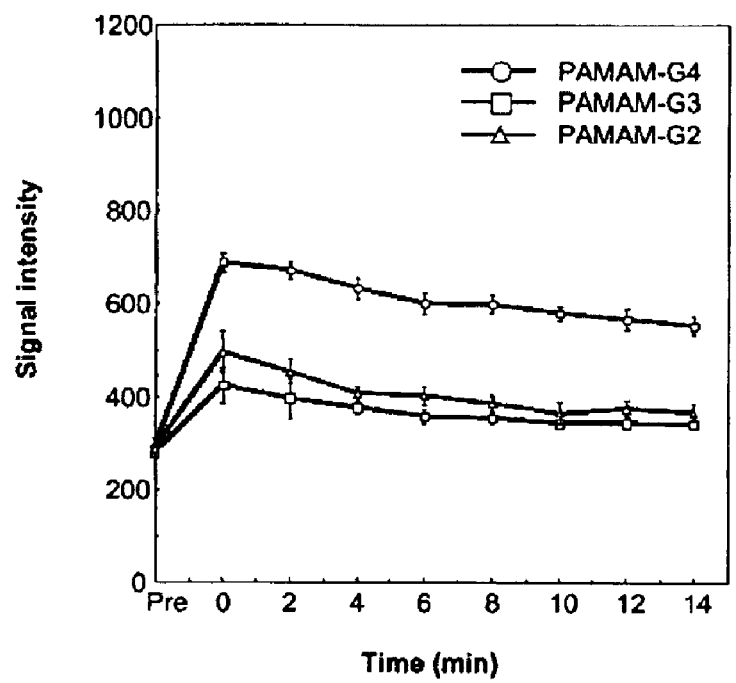
Figure 5F:
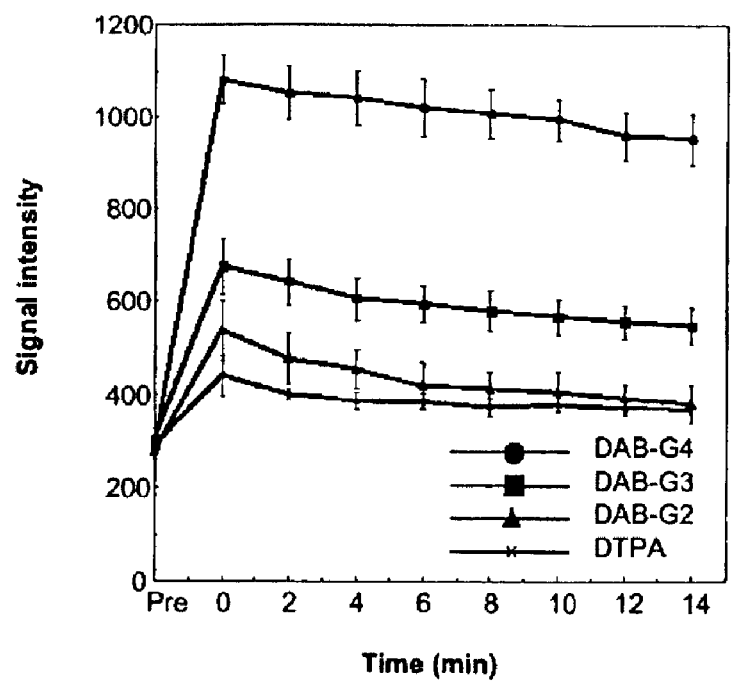

The relative MRI signal intensities of various organs with the whole body images were followed for 15 minutes after administration of the contrast agents. The signal intensity in the left ventricle of the heart was highest for PAMAM-G4 at all times, reflecting its increased retention in the blood volume relative to the other contrast agents (FIGS. 5a–b). On the other hand, the liver signal-intensity values were significantly higher with the DAB-based agents than with the PAMAM-based agents of the same dendrimer generation (p<0.001) at all time points examined (FIGS. 5c–d). In surprising contrast to the biodistribution patterns discussed above in Example 2, the kidney signal-intensity values obtained from the DAB-based agents were also significantly higher than those obtained with the PAMAM-based agents of the same dendrimer generation (p<0.001) within 10 min post-injection (FIGS. 5e–f).

High-resolution coronal images made using the dendrimer-Gd conjugates all exhibited a bright white band at the outer stripe of the outer medulla (FIG. 6a–f). This image enhancement pattern is believed to reflect uptake of the contrast agents by the proximal straight tubules, and may be used to detect acute renal failure (See, Kobayashi et al, "Renal tubular damage detected by dynamic micro-MRI with a dendrimer-based magnetic resonance contrast agent," *Kidney International*, 61: 1980–1985 (2002)). For example, cisplatin induced acute renal failure may be correlated with loss of the bright white band. The bright band was not observed following injection of Gd-[DTPA]-dimeglumine (FIGS. 6g–h).

The size and internal structure of the dendrimers had important effects on whole body retention and MRI imaging characteristics. A significantly larger amount of the DAB-based agents accumulated in the liver as compared to the same generation PAMAM-based agents as indicated by both pharmacokinetic studies with $^{153}$Gd-labeled agents and by the intensity-time curves obtained from the MRI studies. In contrast, a significantly smaller amount of the DAB-based agents accumulated in the kidney as compared to the same generation PAMAM-based agents in the pharmacokinetic studies. Nonetheless, the DAB-based agents exhibited a significantly higher signal-intensity than the same generation of PAMAM-based agents in the kidney, particularly at the early time points of the dynamic studies. Since the DAB-based agents were excreted into the urine more efficiently than the PAMAM-based agents, the high MRI signal obtained may be a consequence of a high concentration of Gd(III) ions in the urine, passing through the kidney within 15 min post-injection. That the pattern of image enhancement for the kidneys is retained for all the dendrimer conjugates is surprising in view of the very different biodistribution, whole-body retention and time-intensity curves observed for these agents.

The proximal straight tubule of the kidney was visualized with all of the dendrimer-Gd conjugates, but was not visualized even when employing a double dose (0.06 mmol Gd/kg) of Gd-[DTPA]-dimeglumine. Attempts to use higher doses (e.g., 0.1 mmol Gd/kg) of Gd-[DTPA]-dimeglumine, resulted in loss of signal from the renal pelvis region because of high concentrations of Gd(III). Taken together, these studies demonstrate that size and internal repeat unit structures of the dendrimer can have a profound influence on in vivo pharmacokinetics, but surprisingly, without changing the actual MRI imaging properties for visualizing renal tubular function.

For use in clinical practice, macromolecular MR contrast agents must be efficiently and rapidly excreted to minimize the potential toxicity of these agents, mostly caused by free Gd(III). Renal filtration and excretion is usually considered to be the optimal route to remove circulating molecules from the body, because they can be eliminated intact without cellular metabolism or processing. However, filtered macromolecules could be reabsorbed by the proximal straight tubules, and then retained within the cells. Smaller MR contrast agents are generally considered to be safer, because they are more rapidly cleared, and have less cellular uptake, a property that may be expected to lead to reduced visualization of proximal straight tubules. Surprisingly, however, the results outlined above demonstrate that, despite their lower whole-body retention, the smaller dendrimer-Gd conjugates (e.g. DAB-G2, DAB-G3 and PAMAM-G2) nevertheless may be used to obtain detailed renal structural/functional information.

In conclusion, all six dendrimer-1B4M-Gd conjugates visualized the renal proximal straight tubules, despite large differences in renal excretion rates. Since the PAMAM-G2D, DAB-G3D, and DAB-G2D based contrast agents were also most rapidly excreted from the body, these three conjugates may be the most acceptable for use in clinical practice.

EXAMPLE 4

Contrast-Enhanced Dynamic 3D-Micro-MRI of Mice with Chronic Renal Failure

To determine if dendrimer-enhanced MR imaging according to the disclosure could detect chronic kidney failure and renal cysts, serial dynamic MR images of normal and 7 month old COX-2 knock-out mice (n=4) were obtained. The later mice have renal cysts and chronic renal failure. The contrast-enhanced dynamic MRI scans were obtained using the fast spoiled gradient echo technique (efgre3d; TR/TE 20.4/7.2; TI49; flip angle 30°; scan time 1'52"; phase encoding steps 512×256; 3 NEX; slab thickness 16) with fat-suppression technique following intravenous injection of 0.03 mmol Gd/kg G4-(1B4M-Gd)64. Serial multi-slice 3D data was obtained over a period of 14 min post-injection of the contrast agents for all mice studied. The width of the cortex and outer stripe of the outer medulla were measured. The combined width of the cortex and outer medulla measured by PAMAM-G4 enhanced MR imaging was much smaller in COX-2 knockout mice (left) than normal mice (right), and correlated with histological thickness (obtained at the time of sacrifice). The differences observed between the normal and COX-2 knockout mice are illustrated in FIG. 7, which shows MRI images at 9 min post-injection. These images show the thicker width of the cortex and outer medulla in the normal mice (FIG. 7a) in comparison to the COX-2 knockout mice (FIG. 7b). COX-2 mice are known to develop small cysts, and FIG. 7b shows that contrast-enhanced MR imaging can detect small cysts. Thus, contrast-enhanced dynamic 3D-micro-MR imaging can be used to detect chronic renal failure and renal cysts.

In view of the many possible embodiments to which the principles of our inventions may be applied, it should be recognized that the illustrated embodiments are only examples of the inventions and should not be taken as a limitation on the scope of the inventions. Rather, the scope of the inventions is defined by the following claims. We therefore claim as our inventions, all that comes within the scope and spirit of these claims.

We claim:

1. A dendrimer conjugate, comprising:
   a dendrimer selected from the group consisting of DAB-G2D and DAB-G3D; and
   a gadolinium (III) chelate of 1B4M.

2. A method for kidney imaging, comprising:
   administering an image enhancing amount of a dendrimer conjugate to a subject, the dendrimer conjugate comprising a dendrimer selected from the group consisting of DAB-G2D, DAB-G3D, DAB-G4D, PAMAM-G2D, PAMAM-G3D and PAMAM-G4D and a metal chelate;
   detecting a difference in a magnetic resonance signal intensity of at least a portion of the kidney after the dendrimer conjugate is administered; and
   measuring a thickness of the cortex and the outer medulla of the kidney in an MRI image to determine if the kidney exhibits thinning associated with chronic renal failure.

3. The method of claim 2, wherein the dendrimer is selected from the group consisting of DAB-G2D, DAB-G3D and PAMAM-G2D.

4. The method of claim 3, wherein the dendrimer is selected from the group consisting of DAB-G2D and DAB-G3D.

5. The method of claim 2, wherein the metal chelate is selected from the group consisting of metal chelates of diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3 A), 1-oxa-4,7, 10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N (2-aminoethyl)amide and DOTA-N-(2-aminophenethyl) amide, BOPTA, HP-DO3A, DO3MA, and derivatives and combinations thereof.

6. The method of claim 2, wherein the metal chelate comprises an ion of a metal selected from the group consisting of the metals having atomic numbers of 22–29, 42, 44 and 58–70 and combinations thereof.

7. The method of claim 6, wherein the ion is selected from the group consisting of chromium (III), manganese (II), iron (II), iron (III), cobalt (II), nickel (II), copper (II), praseodymium (III), neodymium (III), samarium (III), gadolinium (III, terbium (III), dysprosium (III), holmium (III), erbium (III), ytterbium (III) and combinations thereof.

8. The method of claim 7, wherein the ion is gadolinium (III).

9. The method of claim 2, wherein the dendrimer conjugate is a 1B4M conjugate and is selected from the group consisting of DAB-G2, DAB-G3, DAB-G4, PAMAM-G2, PAMAM-G3, PAMAM-G4 and combinations thereof.

10. The method of claim 2, wherein detecting a difference in a magnetic resonance signal intensity of at least a portion of the kidney comprises detecting a difference in a T1-weigthed signal at a position corresponding to the proximal straight tubules of the kidney.

11. The method of claim 10, further comprising comparing the difference in magnetic resonance signal intensity detected for the subject to a difference in signal intensity detected in a second subject to determine whether the kidneys of the subject and the second subject are similar in structure or function.

12. The method of claim 2, wherein the dendrimer conjugate is administered in a dose between about 0.001 mmol Gd/kg and about 0.10 mmol Gd/kg.

13. The method of claim 2, wherein detecting a difference in a magnetic resonance signal intensity of at least a portion of the kidney comprises detecting a signal associated with the appearance of urine in the pelvis of the kidney as the dendrimer conjugate is excreted.

14. The method of claim 2, further comprising detecting an image associated with the presence of cysts indicative of chronic renal failure.

15. A method for kidney imaging, comprising:
administering to a subject an image enhancing amount of a dendrimer conjugate selected from the group consisting of DAB-G2 and DAB-G3, and combinations thereof; and
detecting a difference in a magnetic resonance signal intensity of at least a portion of the kidney after the dendrimer conjugate is administered.

16. The method of claim 15, wherein detecting a difference in a magnetic resonance signal intensity of at least a portion of the kidney after the dendrimer conjugate is administered comprises detecting a signal associated with an accumulation of the dendrimer conjugate in the proximal straight tubules.

17. The method of claim 16, wherein detecting a signal associated with an accumulation of the dendrimer conjugate in the proximal straight tubules comprises detecting accumulation of the dendrimer conjugate in the outer stripe of the outer medulla of the kidney.

18. The method of claim 15, wherein detecting a difference in a magnetic resonance signal intensity of at least a portion of the kidney after the dendrimer conjugate is administered comprises detecting a signal associated with an accumulation of the dendrimer conjugate in pelvis of the kidney.

19. The method of claim 15, wherein the dendrimer conjugate is administered in a dose between about 0.001 mmol Gd/kg and about 0.10 mmol Gd/kg.

20. The method of claim 19, wherein the dendrimer conjugate is administered in a dose between about 0.003 mmol Gd/kg and about 0.03 mmol Gd/kg.

21. The method of claim 15, further comprising measuring the thickness of the cortex and outer medulla of the kidney in an MRI image to determine if the kidney exhibits thinning associated with chronic renal failure.

22. The method of claim 15, further comprising detecting an image associated with the presence of cysts indicative of chronic renal failure.

23. A method for kidney imaging, comprising:
administering an image enhancing amount of a dendrimer conjugate to a subject, the dendrimer conjugate comprising a dendrimer selected from the group consisting of DAB-G2D, DAB-G3D, DAB-G4D, PAMAM-G2D, PAMAM-G3D and PAMAM-G4D and a metal chelate;
detecting a difference in a magnetic resonance signal intensity of at least a portion of the kidney after the dendrimer conjugate is administered; and
detecting an image associated with the presence of cysts indicative of chronic renal failure.

24. The method of claim 23, wherein the dendrimer is selected from the group consisting of DAB-G2D, DAB-G3D and PAMAM-G2D.

25. The method of claim 24, wherein the dendrimer is selected from the group consisting of DAB-G2D and DAB-G3D.

26. The method of claim 23, wherein the metal chelate is selected from the group consisting of metal chelates of diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N (2-aminoethyl)amide and DOTA-N-(2-aminophenethyl) amide, BOPTA, HP-DO3A, DO3MA, and derivatives and combinations thereof.

27. The method of claim 23, wherein the metal chelate comprises an ion of a metal selected from the group consisting of the metals having atomic numbers of 22–29,42,44 and 58–70 and combinations thereof.

28. The method of claim 27, wherein the ion is selected from the group consisting of chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), ytterbium (III) and combinations thereof.

29. The method of claim 28, wherein the ion is gadolinium (III).

30. The method of claim 23, wherein the dendrimer conjugate is a 1B4M conjugate and is selected from the group consisting of DAB-G2, DAB-G3, DAB-G4, PAMAM-G2, PAMAM-G3, PAMAM-G4 and combinations thereof.

31. The method of claim 23, wherein detecting a difference in a magnetic resonance signal intensity of at least a portion of the kidney comprises detecting a difference in a T1-weigthed signal at a position corresponding to the proximal straight tubules of the kidney.

32. The method of claim 31, further comprising comparing the difference in magnetic resonance signal intensity detected for the subject to a difference in signal intensity detected in a second subject to determine whether the kidneys of the subject and the second subject are similar in structure or function.

33. The method of claim 23 wherein the dendrimer conjugate is administered in a dose between about 0.001 mmol Gd/kg and about 0.10 mmol Gd/kg.

34. The method of claim 23, wherein detecting a difference in a magnetic resonance signal intensity of at least a portion of the kidney comprises detecting a signal associated with the appearance of urine in the pelvis of the kidney as the dendrimer conjugate is excreted.

35. The method of claim 23, further comprising measuring a thickness of the cortex and outer medulla of the kidney in an MRI image to determine if the kidney exhibits thinning associated with chronic renal failure.

36. A method for kidney imaging, comprising:
administering an image enhancing amount of a dendrimer conjugate to a subject, the dendrimer conjugate comprising a dendrimer selected from the group consisting of DAB-G2D and DAB-G3D and a metal chelate; and
detecting a difference in a magnetic resonance signal intensity of at least a portion of the kidney after the dendrimer conjugate is administered.

37. The method of claim 36, wherein the metal chelate is selected from the group consisting of metal chelates of diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N (2-aminoethyl)amide and DOTA-N-(2-aminophenethyl) amide, BOPTA, HP-DO3A, DO3MA, and derivatives and combinations thereof.

38. The method of claim 36, wherein the metal chelate comprises an ion of a metal selected from the group consisting of the metals having atomic numbers of 22–29, 42, 44 and 58–70 and combinations thereof.

39. The method of claim 38, wherein the ion is selected from the group consisting of chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), ytterbium (III) and combinations thereof.

40. The method of claim 39, wherein the ion is gadolinium (III).

41. The method of claim 36, wherein the dendrimer conjugate is a 1B4M conjugate and is selected from the group consisting of DAB-G2 and DAB-G3 and combinations thereof.

42. The method of claim 36, wherein detecting a difference in a magnetic resonance signal intensity of at least a portion of the kidney comprises detecting a difference in a T1-weigthed signal at a position corresponding to the proximal straight tubules of the kidney.

43. The method of claim 42, further comprising comparing the difference in magnetic resonance signal intensity detected for the subject to a difference in signal intensity detected in a second subject to determine whether the kidneys of the subject and the second subject are similar in structure or function.

44. The method of claim 36, wherein the dendrimer conjugate is administered in a dose between about 0.001 mmol Gd/kg and about 0.10 mmol Gd/kg.

45. The method of claim 36, wherein detecting a difference in a magnetic resonance signal intensity of at least a portion of the kidney comprises detecting a signal associated with the appearance of urine in the pelvis of the kidney as the dendrimer conjugate is excreted.

46. The method of claim 36, further comprising measuring a thickness of the cortex and outer medulla of the kidney in an MRI image to determine if the kidney exhibits thinning associated with chronic renal failure.

47. The method of claim 36, further comprising detecting an image associated with the presence of cysts indicative of chronic renal failure.

48. A method for kidney imaging comprising:
administering to a subject an image enhancing amount of a dendrimer conjugate selected from the group consisting of DAB-G2, DAB-G3, PAMAM-G2 and combinations thereof;
detecting a difference in a magnetic resonance signal intensity of at least a portion of the kidney after the dendrimer conjugate is administered; and
measuring a thickness of the cortex and outer medulla of the kidney in an MRI image to determine if the kidney exhibits thinning associated with chronic renal failure.

49. A method for kidney imaging, comprising:
administering to a subject an image enhancing amount of a dendrimer conjugate selected from the group consisting of DAB-G2, DAB-G3, PAMAM-G2 and combinations thereof;
detecting a difference in a magnetic resonance signal intensity of at least a portion of the kidney after the dendrimer conjugate is administered; and
detecting an image associated with the presence of cysts indicative of chronic renal failure.

* * * * *